US00PP23191P3

(12) United States Plant Patent
Klemm et al.

(10) Patent No.: US PP23,191 P3
(45) Date of Patent: Nov. 13, 2012

(54) ***CALIBRACHOA* PLANT NAMED 'KLECA09204'**

(50) Latin Name: ***Calibrachoa* hybrid**
Varietal Denomination: KLECA09204

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 282 days.

(21) Appl. No.: 12/661,880

(22) Filed: Mar. 25, 2010

(65) Prior Publication Data

US 2011/0239343 P1 Sep. 29, 2011

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP21,018 P2 * 5/2010 Klemm et al. ..... Plt./413

OTHER PUBLICATIONS

Anonymous. 2012 Selecta Catalog. See particularly pp. 18-61. Publication date unknown, accessed Jul. 12, 2011.*
UPOV ROM GTITM Computer Database, GTI Jouve Retrieval Software 2011/03 CA Citation for 'KLECA09204'.*
UPOV ROM GTITM Computer Database, GTI Jouve Retrieval Software 2011/03 QZ Citation for 'KLECA09204'.*
UPOV PLUTO Citation for 'KLECA11225' Accessed Aug. 13, 2012.*

* cited by examiner

*Primary Examiner* — Wendy C Haas
(74) *Attorney, Agent, or Firm* — Jondle & Associates, P.C.

(57) ABSTRACT

A new *Calibrachoa* plant named 'KLECA09204' particularly distinguished by double flowers with more than five petals, a very early flowering time, a compact mounding plant habit, and continuously rich flowering with very good heat and rain tolerance, is disclosed.

1 Drawing Sheet

Genus and species: *Calibrachoa* hybrid.
Variety denomination: 'KLECA09204'.

BACKGROUND OF THE NEW PLANT

The present invention comprises a new and distinct variety of *Calibrachoa,* botanically known as *Calibrachoa* hybrid and hereinafter referred to by the variety name 'KLECA09204'. The new variety was discovered as a seedling resulting from a cross conducted in June 2006 in Stuttgart, Germany. The female parent was the proprietary *Calibrachoa* plant 'KLECA08182' (U.S. Plant Pat. No. 21,018), while the male parent was the proprietary *Calibrachoa* plant 'KLECA06098' (now abandoned U.S. Plant patent application Ser. No. 12/002,478).

The new variety was first propagated via vegetative cuttings in May 2007 in Stuttgart, Germany and has been asexually reproduced by vegetative propagation cuttings and in-vitro propagation by tissue culture of shoot tips in Stuttgart, Germany for more than 60 generations. The present invention has been found to retain its distinctive characteristics through successive asexual propagations.

Plant Breeder's Rights for this variety have been applied for in Canada on Mar. 25, 2009. 'KLECA09204' has not been made publicly available or sold more than one year prior to the filing date of this application.

SUMMARY OF THE INVENTION

The following are the most outstanding and distinguishing characteristics of this new variety when grown under normal horticultural practices in Stuttgart, Germany.

1. Double flowers with more than five petals;
2. A very early flowering time;
3. A compact mounding plant habit; and
4. Continuously rich flowering with very good heat and rain tolerance.

DESCRIPTION OF THE PHOTOGRAPH

This new *Calibrachoa* plant is illustrated by the accompanying photograph which shows flowers and foliage of the plant. The colors shown are as true as can be reasonably obtained by conventional photographic procedures. The photograph was taken in May 2009 of a 5-month old *Calibrachoa* plant, grown in a glass greenhouse in Stuttgart, Germany.

DESCRIPTION OF THE NEW VARIETY

The following detailed descriptions set forth the distinctive characteristics of 'KLECA09204'. The data which defines these characteristics were collected from asexual reproductions carried out in Stuttgart, Germany. The plant history was taken in May 2009 on 5-month old plants which were planted as rooted cuttings in 11.0 centimeter pots and then grown in a glass greenhouse. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
*Family.*—Solanaceae.
*Botanical.*—*Calibrachoa* sp.

*Denomination.*—'KLECA09204'.

*Common.*—*Calibrachoa Hybrida.*

Parentage:

*Female.*—The proprietary *Calibrachoa* plant 'KLECA08182' (U.S. Plant Pat. No. 21,018).

*Male.*—The proprietary *Calibrachoa* plant 'KLECA06098' (now abandoned U.S. Plant patent application Ser. No. 12/002,478).

Growth:

*Form.*—Uniformly mounded.

*Habit.*—Semi-upright, compact and tight.

*Height* (*measured from the top of the soil*).—6.0 cm to 8.0 cm.

*Width* (*horizontal plant diameter*).—17.0 cm.

*Time to produce a finished flowering plant.*—7 to 8 weeks.

*Outdoor plant performance.*—Continuously flowering, healthy, good rain tolerance.

*Time to initiate and develop roots.*—18 days.

*Root description.*—Fine, fibrous, freely branching, moderately dense, white roots.

Stems:

*Length of basal branches.*—7.0 cm.

*Internode length.*—0.6 cm to 1.0 cm.

*Diameter of branches* (*from midpoint*).—6.0 cm.

*Stem color.*—RHS 145A.

*Texture.*—Smooth.

*Anthocyanin.*—Absent.

*Pedicel.*—Color: RHS 145C. Length: 0.9 cm. Diameter: 0.1 cm. Texture: Smooth.

Leaves:

*Arrangement.*—Alternate, simple, sessile.

*Size.*—Length: 1.5 cm to 2.5 cm. Width: 0.5 cm to 0.8 cm.

*Shape.*—Lanceolate to elliptic.

*Apex.*—Obtuse to slightly acute.

*Base.*—Attenuate.

*Margin.*—Entire.

*Color* (*both immature and mature leaves*).—Upper surface: RHS 144A. Lower surface: RHS 144B.

*Texture* (*both upper and lower surfaces*).—Smooth.

*Venation pattern.*—Pinnate.

*Petioles.*—Absent, sessile.

Flower bud:

*Shape.*—Oblong.

*Size.*—Length: 1.7 cm. Diameter: 0.7 cm.

*Color at tight bud.*—RHS 2B.

Inflorescence:

*Blooming habit.*—Flowers face upright, double flowering, axillary.

*Inflorescence type.*—Determinate inflorescence.

*Floret type.*—Double flower.

*Lastingness of individual blooms on the plant.*—6 days.

*Fragrance.*—Absent.

Flowers:

*Immature flower.*—Diameter: Horizontal: 2.0 cm. Vertical: 2.0 cm. Color: Upper surface: RHS 5B. Lower surface: RHS 5C.

*Mature flower.*—Diameter: Horizontal: 2.3 cm. Vertical: 2.0 cm. Color: Upper surface: RHS 6A. Lower surface: RHS 6D.

*Corolla tube.*—Color inside: RHS 12B. Color outside: RHS 12C. Tube length: 1.5 cm. Texture (both outside and inside): Smooth.

*Petals.*—Apex: Obverse. Base: Open, fused into the tube. Margin: Entire. Waviness of petals: Very weak. Location: Very weak. Texture (both upper and lower surfaces): Smooth.

*Sepals.*—Calyx (composition): Actinomorphic. Shape: Lanceolate to elliptic. Apex: Acute. Base: Open, tube fused into the base. Margin: Entire. Length: 1.1 cm. Width: 0.2 cm. Color: Upper surface: RHS 144C. Lower surface: RHS 144B. Texture (both upper and lower surfaces): Smooth.

Reproductive organs:

*Stamens.*—Absent.

*Pistils.*—Number: 1. Length: 1.2 cm. Diameter: 0.1 cm. Stigma color: RHS 145B.

*Style color.*—RHS 145B.

Fruit and seed set: No fruit and seed set observed.

Disease and insect resistance: No particular resistance or susceptibility has been observed.

COMPARISON WITH PARENTAL AND COMMERCIAL VARIETIES

'KLECA09204' differs from the female parent *Calibrachoa* plant 'KLECA08182' (U.S. Plant Pat. No. 21,018), in that 'KLECA09204' has larger flowers than 'KLECA08182'.

'KLECA09204' differs from the male parent *Calibrachoa* plant 'KLECA06098' (now abandoned U.S. Plant patent application Ser. No. 12/002,478), in that 'KLECA09204' has double flowers, whereas 'KLECA06098' has single flowers.

'KLECA09204' differs from the commercial variety *Calibrachoa* MiniFamous Yellow, also known as 'KLECA11225' (unpatented), in that 'KLECA09204' has a flower color of RHS 6A, whereas 'KLECA11225' has a flower color of RHS 9A.

We claim:

1. A new and distinct variety of *Calibrachoa* plant named 'KLECA09204' as shown and described herein.

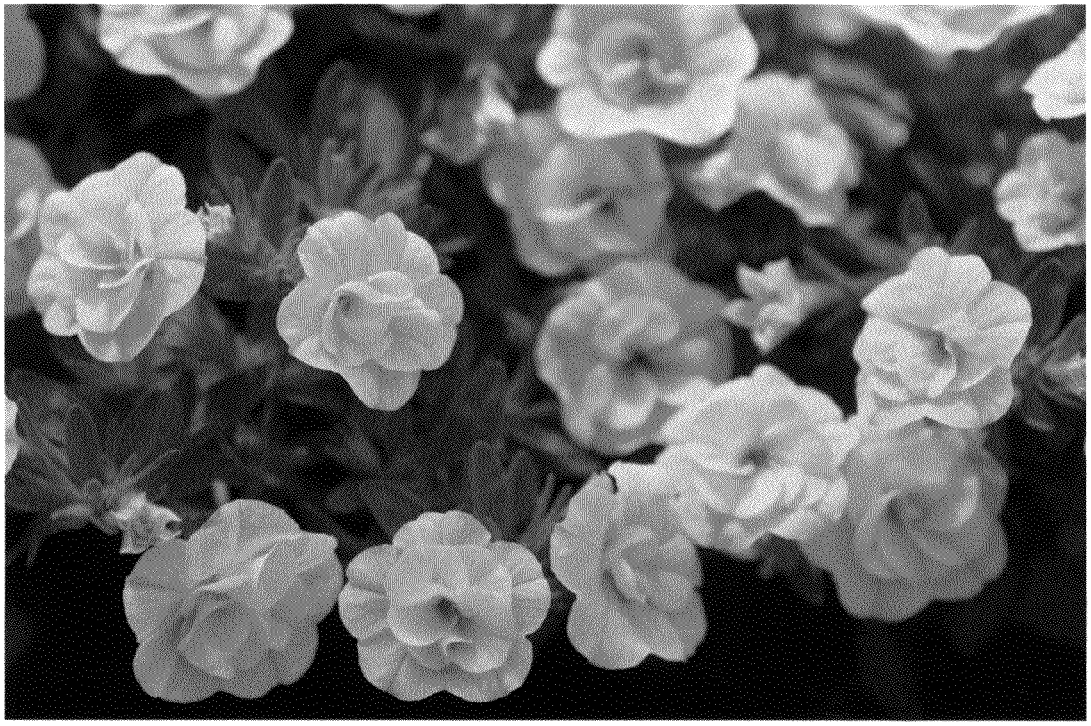

* * * * *